(12) United States Patent
Love (10) Patent No.: US 9,718,801 B2
(45) Date of Patent: Aug. 1, 2017

(54) APPARATUS AND METHOD FOR VIBRATIONAL ISOLATION OF COMPOUNDS

(71) Applicant: J P Love, Nevada City, CA (US)

(72) Inventor: J P Love, Nevada City, CA (US)

(73) Assignee: JP LOVE, Nevada City, CA (US)

( * ) Notice: Subject to any disclaimer, the term of this patent is extended or adjusted under 35 U.S.C. 154(b) by 0 days.

(21) Appl. No.: 14/404,433

(22) PCT Filed: Jul. 1, 2013

(86) PCT No.: PCT/US2013/048939
§ 371 (c)(1),
(2) Date: Nov. 26, 2014

(87) PCT Pub. No.: WO2014/008192
PCT Pub. Date: Jan. 9, 2014

(65) Prior Publication Data
US 2015/0166502 A1    Jun. 18, 2015

Related U.S. Application Data

(60) Provisional application No. 61/666,913, filed on Jul. 1, 2012.

(51) Int. Cl.
| | |
|---|---|
| *A61K 36/185* | (2006.01) |
| *C07D 311/80* | (2006.01) |
| *B01D 21/02* | (2006.01) |
| *B01D 11/02* | (2006.01) |
| *B01F 11/00* | (2006.01) |
| *B01F 11/02* | (2006.01) |

(52) U.S. Cl.
CPC ........ *C07D 311/80* (2013.01); *B01D 11/0261* (2013.01); *B01D 21/02* (2013.01); *B01F 11/0094* (2013.01); *B01F 11/0266* (2013.01); *A61K 36/185* (2013.01); *A61K 2236/00* (2013.01)

(58) Field of Classification Search
None
See application file for complete search history.

(56) References Cited

U.S. PATENT DOCUMENTS

| | | |
|---|---|---|
| 2002/0039795 A1 | 4/2002 | Elsohly et al. |
| 2004/0262213 A1 | 12/2004 | Kirker et al. |
| 2007/0184541 A1 | 8/2007 | Karl et al. |
| 2011/0098348 A1 | 4/2011 | De Meijer |
| 2011/0256245 A1 | 10/2011 | Rosenblatt et al. |

FOREIGN PATENT DOCUMENTS

| | | |
|---|---|---|
| CA | 889155 | 12/1971 |
| GB | 2459125 | 10/2009 |
| RU | WO9923260 | 5/1999 |
| WO | WO9527551 | 10/1995 |
| WO | WO2008109304 | 9/2008 |

OTHER PUBLICATIONS

Website document entitled: "Bubble Hash & THC Extraction (How to make Bubble Hash—How to Press Bubble Hash)" (available at http://www.informationon.com/bubble-hash-hashish). Downloaded from website: Aug. 15, 2012.*
The website document entitled: "How to Make Wicked Hash" (available at http://www.cannibisculture.com/content/hown-make-wicked-hash). Downloaded from website Aug. 15, 2012.*
International Search Report, Application No. PCT/US2013/048939, Feb. 20, 2014, 18 pages.
eESR PCT/US2013/048939, May 4, 2016, 8 pages.

* cited by examiner

*Primary Examiner* — Chris R Tate
*Assistant Examiner* — Russell Fiebig
(74) *Attorney, Agent, or Firm* — Sci-Law Strategies, PC (57) ABSTRACT

The present invention is directed to a method and device to isolate compounds from plant material using vibrational pulsing, vibrational decanting, vibrational sieving and vibrational rinsing. A susceptible liquid is generated by vibrational agitation, decanted when in a vibrating container and then collected by passing over a series of vibrating screens and then rinsed with water while collected on the vibrating screens and the residue collected. The isolated compound can either be collected in the decant or retained on the screens. In an embodiment of the invention, the vibrational rinsing step reduces unwanted impurities isolated.

16 Claims, 6 Drawing Sheets

APPARATUS AND METHOD FOR VIBRATIONAL ISOLATION OF COMPOUNDS

PRIORITY CLAIM

This application is a national phase application of and claims priority to (1) PCT patent publication number WO2014/008192, entitled "Apparatus and Method for Vibrational Sieving of Compounds", inventor: J. P. Love, filed Jul. 1, 2013 as patent application number PCT/US13/48939 which claims priority to (2) U.S. Provisional Application No. 61/666,913 entitled "Apparatus and Method for Vibrational Sieving of Compounds", inventor: J. P. Love filed Jun. 28, 2010. Each of these applications (1)-(2) are herein expressly incorporated by reference in their entirety.

FIELD OF THE INVENTION

The present invention relates to methods and devices for isolating or purifying plant trichomes, resin ducts, subdermal oil glands and/or other plant organic compounds through vibrational sieving.

BACKGROUND OF THE INVENTION

The kingdom Plantae contains 12 phylum or divisions. Plantae includes familiar organisms such as flowering plants, conifers, ferns, mosses, and green algae, but do not include seaweeds like kelp, nor fungi and bacteria. The group is also called green plants or Viridiplantae in Latin. Species within Plantae obtain most of their energy from sunlight via photosynthesis using chlorophyll contained in chloroplasts, which gives them their green color. There are thought to be three hundred thousand species of plants, of which the great majority are seed plants. The kingdom Fungi encompasses a broad diversity of taxa with varied ecologies, life cycle strategies, and morphologies ranging from single-celled aquatic chytrids to large mushrooms. The kingdom Fungi has been estimated at over one million species, but less than 5% having been formally classified.

Aromatherapy is a form of alternative medicine that uses volatile compounds present in plant material as a treatment. The volatile compounds are often isolated as an oil which can then be heated and the aroma from the heated oil can be inhaled. Tea tree belongs to the Myrtaceae family and include *Melaleuca alternifolia, M. cajuptii; M. viridflora* and *M quiquenervia vividflora*. Other plants belonging to the Myrtaceae family include cajeput, niaouli, clove, *eucalyptus* and myrtle. Oils isolated from Myrtaceae family plants are used in aromatherapy and have been demonstrated to have anti-infectious and anti-microbial effects. The principal constituents in tea tree oil include terpinen-4-ol, alpha-terpineol, cineole, pinene, alpha terpene, beta-caryopyllene and cymene.

Extracts from Cannabaceae or Hemp family plants (generic name *Cannabis*) were adopted in eastern Asian herbal remedies before 2700 B.C. *Cannabis* plants include *Cannabis sativa, C. indica* and *C. ruderalis*. The *Cannabis* seed was cultivated at least by the Chinese. The active ingredient includes 3,4-trans-delta-1-tetrahydrocannabinol (THC), a psychoactive hallucinogenic compound which binds to the Cannabinoid (CB) receptor present in the brain cerebral cortex and stimulates euphoria and modified sensual perceptions. Hashish is a resin collected by thrashing flowering tops against a smooth rock where the sap will stick and can be collected. While ingestion of hashish and either chewing and/or ingestion of *Cannabis* leaves has been recorded at various points through history, the liver 'sloughs off' the THC thereby reducing the THC effect and damaging the renal cells. More commonly, beverages were brewed to extract the THC and other cannabinoids. Dutch colonials in South Africa adapted the *Cannabis* plant by drying the leaves and then incinerating the leaves (smoking) and inhaling the smoke directly. Alternatively, vaporization can be used to extract the THC and reduce irritating toxic and carcinogenic by-products. Incineration or vaporization releases the gaseous THC which when inhaled can be absorbed through the lungs into the blood stream to act on the CB receptor. An alternative means of obtaining the effects of THC involves mixing the *Cannabis* leaves with alcohol to form an infusion which can then be consumed as an alcoholic beverage. Alternatively, THC can be extracted into butter or oil by mixing and mild heating, then the butter or oil can be used in baking and the baked goods consumed.

A one-gram cigarette containing 10 mg of THC (1% by weight) is considered psychoactive. The concentration of THC in *Cannabis* leaves can range from 1-5% by weight. Hashish resin can have up to 60% THC by weight. Extractions from *Cannabis* leaves using organic solvents such as methanol, ethanol, benzene, butanol, petroleum ether, or isopropyl alcohol can produce yields of 1-18% by weight (depending on whether buds of leaves are used), however the purity of the THC depends on the solvent used for the extraction. For example, butane is relatively non polar and does not extract the water soluble substances in the leaves such as chlorophyll and the alkaloids compared with more polar alcohols. A characteristic of all non-aqueous solvent methods of extraction is that they remove lipid soluble inactive material consisting of plant cell constituents including but not limited to fats, waxes, carbohydrates, proteins and sugars from the plant material.

There are over 300 known compounds in *Cannabis* of which more than 50 are related to or have the cannabinoid structure. However, cannabidiols are generally only mildly active and the cannabinols are generally not psychoactive. The psychoactive compounds are present on the leaves and in resin produced from special glandular trichomes on the plant surface. The roots and stem do not have the psychoactive compounds. Trichomes on plants are epidermal outgrowths of various kinds. A hair is a common type of trichome. Plant hairs can be unicellular or multicellular, branched or un-branched. Multicellular hairs can have one or several layers of cells. Branched hairs can be dendritic, tufted, or stellate. A common type of trichome is the scale or peltate hair: a plate or shield shaped cluster of cells attached directly to the surface. Any of the various types of hairs can be glandular. In describing the surface appearance of plant organs many terms are used in reference to the presence, form, and appearance of trichomes including: glabrous, lacking hairs or smooth surface; hirsute, coarsely hairy; hispid, having bristly hairs; downy, having an almost wool like covering of long hairs; pilose, pubescent with long, straight, soft, spreading or erect hairs; pubescent, bearing hairs of any type; strigose, having straight hairs all pointing in more or less the same direction as along a margin or midrib; tomentose, covered with dense, matted, woolly hairs; and villous, having long, soft curved, but not matted hairs. Trichomes are extremely variable in their presence across species, location on plant organs, density (even within a species), and therefore functionality. However, several basic functions or advantages of having surface hairs include: interference with the feeding of at least some small herbivores and, depending upon stiffness and irritability to the "palate", large herbivores as well; keeping frost away from the living surface cells; breaking-up the flow of air across the plant surface, and reducing evaporation; protecting the more delicate tissues underneath in hot, dry, open habitats; and attracting available moisture from cloud drip.

SUMMARY OF THE INVENTION

In an embodiment of the present invention, mixing plant material with water in a washing machine and vibrating is used to generate a susceptible liquid, which is then vibration decanted and the decant is passed through a series of vibrating screens to isolate and/or purify an organic component from plant material present in the susceptible liquid. In an embodiment of the present invention, passing chilled water over the series of screens while continuing to apply the vibrational force to the series of screens can be used to further purify the organic component isolated on the screens. In an embodiment of the present invention, generating a susceptible liquid by mixing plant material with a liquid in a washing machine and then decanting the susceptible liquid and passing the decant through a series of vibrating screens can be used to isolate and/or purify an organic component from plant material present in the susceptible liquid.

BRIEF DESCRIPTION OF THE DRAWINGS

This invention is described with respect to specific embodiments thereof. Additional aspects can be appreciated from the Figures in which.

DETAILED DESCRIPTION OF THE INVENTION

Definitions

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated with a composition.

The transitional phrase "consisting essentially of" limits the scope of a claim to the specified materials or steps and those that do not materially affect the basic and novel characteristic(s) of the claimed invention.

A screen means one or more of a mesh, a closely perforated metal, a series of segments of wire, a series of segments of metal ribbon, a series of segments of metal strand, a series of segments of animal string, a series of segments of paper, perforated paper, a series of segments of fiber, a cloth, a series of segments of silica, a series of segments of plastic, a plastic foam, a series of segments of polymer, a series of segments of Teflon, polymer impregnated teflon, a series of segments of cellulose and includes perforated paper, paper sieves, plastic sieves, and Teflon sieves. In various embodiments of the invention, a screen includes one or more of three or more connected filaments, three or more connected strings, mesh, foam, a grid, perforated paper, and sieves used to strain a susceptible liquid or colloidal dispersion. A 25 micron screen means that the pore of the screen has a dimension of 25 microns. A 1200 mesh would allow particles of less than 12 microns to pass through; a 400 mesh would allow particles of less than 37 microns to pass through; a 325 mesh would allow particles of less than 44 microns to pass through; a 200 mesh would allow particles of less than 74 microns to pass through; a 100 mesh would allow particles of less than 150 microns to pass through; a 60 mesh would allow particles of less than 250 microns to pass through; and a 28 mesh would allow particles of less than 700 microns to pass through.

A metal comprises one or more elements consisting of lithium, beryllium, boron, carbon, nitrogen, oxygen, sodium, magnesium, aluminum, silicon, phosphorous, sulphur, potassium, calcium, scandium, titanium, vanadium, chromium, manganese, iron, cobalt, nickel, copper, zinc, gallium, germanium, arsenic, selenium, rubidium, strontium, yttrium, zirconium, niobium, molybdenum, technetium, ruthenium, rhodium, palladium, silver, cadmium, indium, tin, antimony, tellurium, cesium, barium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, thallium, lead, bismuth, polonium, francium and radium.

A plastic comprises one or more of polystyrene, high impact polystyrene, polypropylene, polycarbonate, low density polyethylene, high density polyethylene, polypropylene, acrylonitrile butadiene styrene, polyphenyl ether alloyed with high impact polystyrene, expanded polystyrene, polyphenylene ether and polystyrene impregnated with pentane, a blend of polyphenylene ether and polystyrene impregnated with pentane or polyethylene and polypropylene.

A polymer comprises a material synthesized from one or more reagents selected from the group comprising of styrene, propylene, carbonate, ethylene, acrylonitrile, butadiene, vinyl chloride, vinyl fluoride, ethylene terephthalate, terephthalate, dimethyl terephthalate, bis-beta-terephthalate, naphthalene dicarboxylic acid, 4-hydroxybenzoic acid, 6-hyderoxynaphthalene-2-carboxylic acid, mono ethylene glycol (1,2 ethanediol), cyclohexylene-dimethanol, 1,4-butanediol, 1,3-butanediol, polyester, cyclohexane dimethanol, terephthalic acid, isophthalic acid, methylamine, ethylamine, ethanolamine, dimethylamine, hexamthylamine diamine (hexane-1,6-diamine), pentamethylene diamine, methylethanolamine, trimethylamine, aziridine, piperidine, N-methylpiperideine, anhydrous formaldehyde, phenol, bisphenol A, cyclohexanone, trioxane, dioxolane, ethylene oxide, adipoyl chloride, adipic, adipic acid (hexanedioic acid), sebacic acid, glycolic acid, lactide, caprolactone, aminocaproic acid and or a blend of two or more materials synthesized from the polymerization of these reagents.

A plastic foam is a polymer or plastic in which a gaseous bubble is trapped including polyurethane, expanded polystyrene, phenolic foam, XPS foam and quantum foam.

Deployed means attached, affixed, adhered, inserted, or otherwise associated. A reservoir is a vessel used to contain one or more of a liquid, a gaseous or a solid sample.

Susceptible material means matter that has come from a once-living organism and is composed of organic compounds. Susceptible material is capable of decay, or is the product of decay. Susceptible material includes cellular matter from one or more of Plantae, Fungus, marine algae, Bacteria and Archae. Isolation from susceptible material is expressed in a dry weight of the substance retrieved by the dry weight of the susceptible material used to extract. When the susceptible material is *cannabis* leaves, 66 percent of the plant weight is water, and the usable dry weight yield (leaf and bud) can be up to 2.3 kg per mature female *cannabis* plant, although the average yield is 448 g per plant. After trimming the wet plant to dry plant product ratio is approximately 14 percent. THC containing material is about 30 percent of the dried plant weight or approximately 10 percent of the wet plant weight. Seeds make up 23 percent of the dry weight and stems (which do not contain significant amounts of THC) 43 percent of the dry weight of the plant. Medical *cannabis* producers typically dry their product to 10 percent moisture content, while street samples can contain 12-16 percent moisture. The approximately 500 g dry weight plant on average produces 0.25 g of bud.

Mixing means making a susceptible liquid containing particles or colloidal dispersion by combining susceptible material with a liquid or gas. When the susceptible material contains molecules or components that can be extracted from the material by water, then the liquid can be water. Other liquids or dispersions can include one or more components selected from the group consisting of water, alcohol, dimethyl sulfoxide, methyl sulfoxide, methyl sulfide, dimethylformamide, tetrahydrofuran and chlorinated or fluorinated hydrocarbons.

Sonication is the act of applying ultrasound energy to agitate particles in a sample to increase the speed by which the particles are extracted from the material by the liquid, by breaking intermolecular interactions. Sonication can be used to remove dissolved gases from liquids when performed under a vacuum. In biological applications, sonication can disrupt or deactivate biological material, e.g., by disrupting cell membranes in order to release the contents of the cell. Sonication is also used to fragment molecules of DNA into smaller fragments.

Vibration sieving is the act of applying a susceptible liquid or susceptible colloidal dispersion to one or more screens upon which vibration forces are applied so that the screen sieves the susceptible liquid or colloidal dispersion to allow the liquid to pass thru and retain the particulate material on the vibrating screen.

Commonly it is thought that *Cannabis* must be dried to remove more than fifty (50) percent of the cannabinoids. A single chloroform extraction for thirty (30) minutes can remove ninety eight (98) percent of the cannabinoids. After filtering, the extract can be chilled to precipitate waxes and then extracted with 2% aqueous sodium sulfate. Odiferous terpenes can be removed by vacuum distillation, which can be purified by column chromatography using alcohol or ether mobile phases. Alternatively, *Cannabis* leaves can be immersed in either methanol, ethanol, benzene, butanol, petroleum ether, or isopropyl alcohol to extract (12 hours), filter and evaporate to give a resin. The extraction can be repeated with fresh solvent. The process can be repeated until no more resin is obtained. Further, *Cannabis* leaves can be decarboxylated by heating to 100 degrees for fifteen minutes. Cannabidiol and cannabidiolic acid can then be extracted with petroleum ether or benzene (50 g leaves/liter of solvent) and allowed to soak for twelve hours with occasional shaking, filtering and extraction with petroleum ether three times with a solution containing 5% NaOH and 5% $Na_2SO_3$. The aqueous extract is then acidified with cold dilute sulfuric acid and extracted with diethylether or $CHCl_3$ which can be dried and evaporated in a vacuum and the residue added to the grass. Cannabidiol and cannabidiolic acid can be converted to THC by boiling in benzene for seven hours.

GB 635,121 describes a process for extracting from aromatic plants by distillation with the help of a hot gas, preferably under high vacuum. WO 99/11311 describes a vaporizer for inhalation and a method for extracting active ingredients from a natural product. This method utilizes an ascending stream of hot air, or a heated inert gas stream, to volatilize components from the natural product and the resultant vapor inhaled. Separation by distillation is a physical process widely used in the preparation of essential oils. Chlorinated solvents are no longer used for extraction of plant biomass because they are toxic and the solvent must be removed. Extraction with supercritical fluid chromatography using $CO_2$ has been used to remove active constituents from foods such as caffeine from coffee beans, and humulene and other flavors from hops (*Humulus lupulus*).

In the following description, various aspects of the present invention will be described. However, it will be apparent to those skilled in the art that the present invention may be practiced with only some or all aspects of the present invention. For purposes of explanation, specific numbers, materials, and configurations are set forth in order to provide a thorough understanding of the present invention. However, it will be apparent to one skilled in the art that the present invention may be practiced without the specific details. In other instances, well-known features are omitted or simplified in order not to obscure the present invention.

EXAMPLES

Figure 1A:
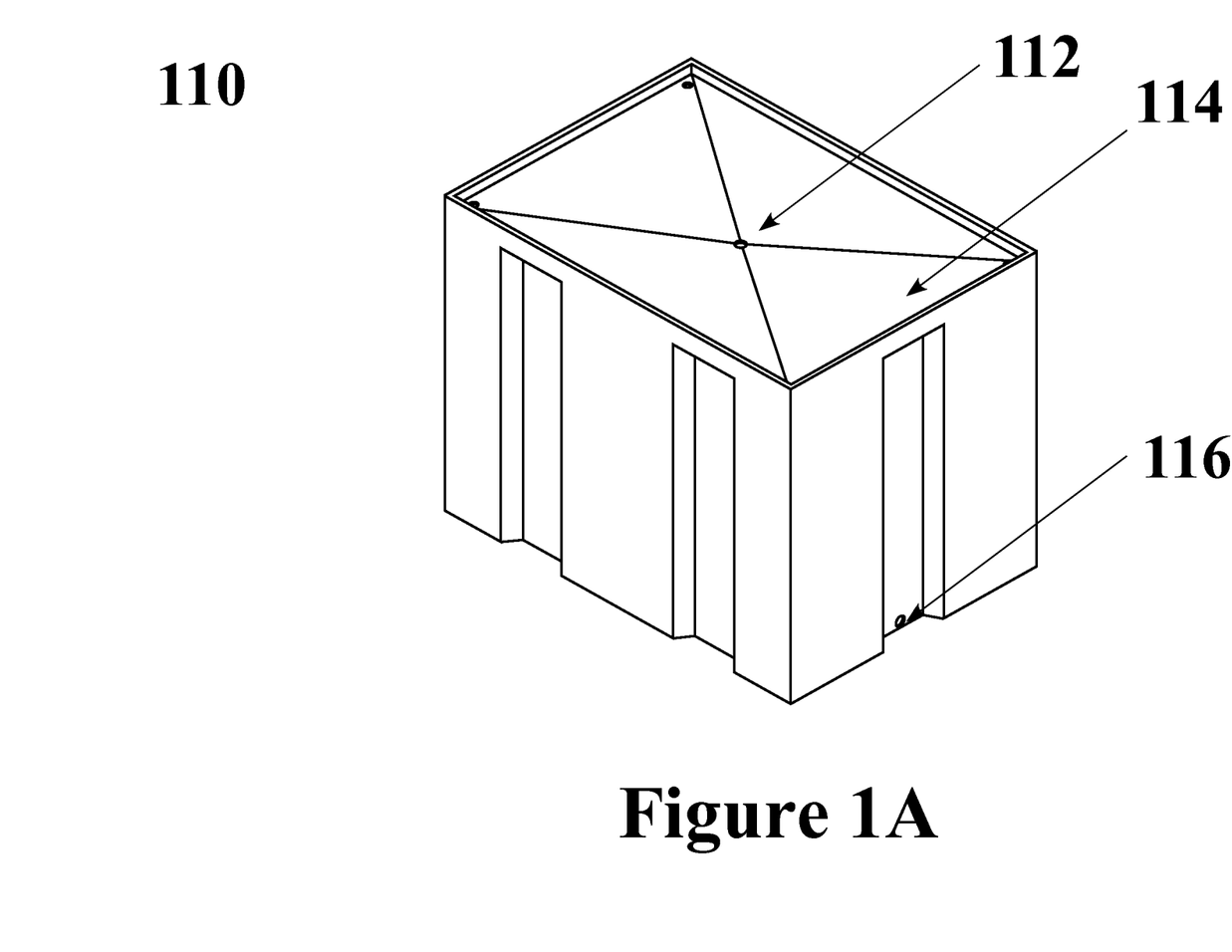
FIG. 1 is a schematic diagram of a 'run-off tank' tank, according to an embodiment of the invention.
Figure 1B:
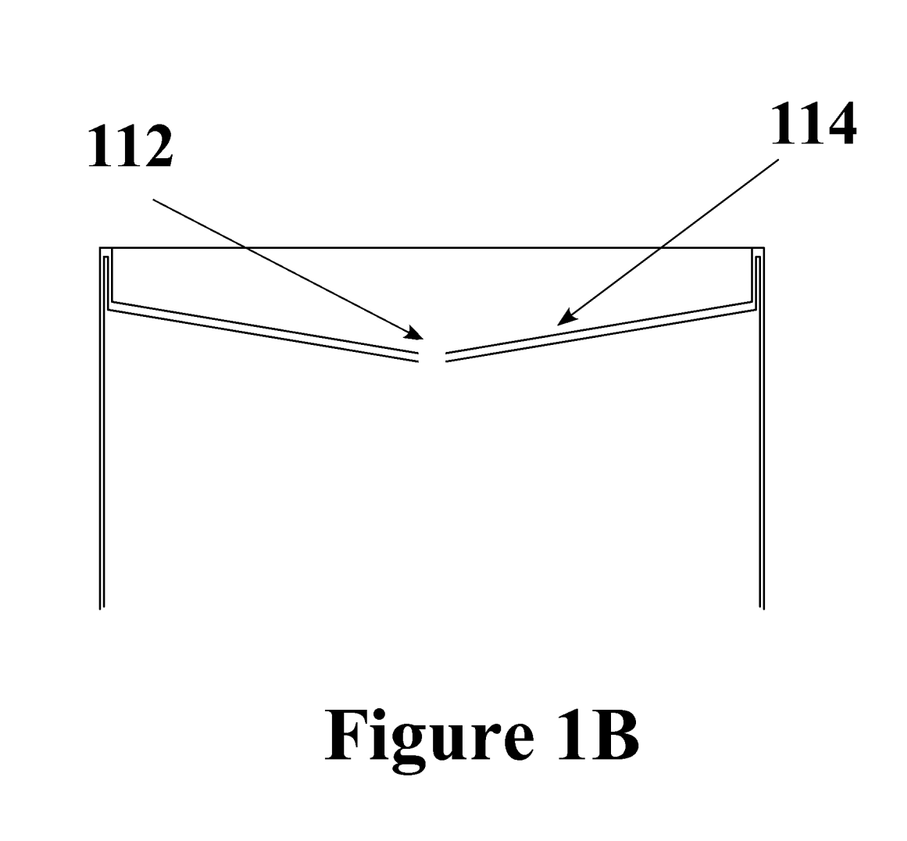
Figure 2A:
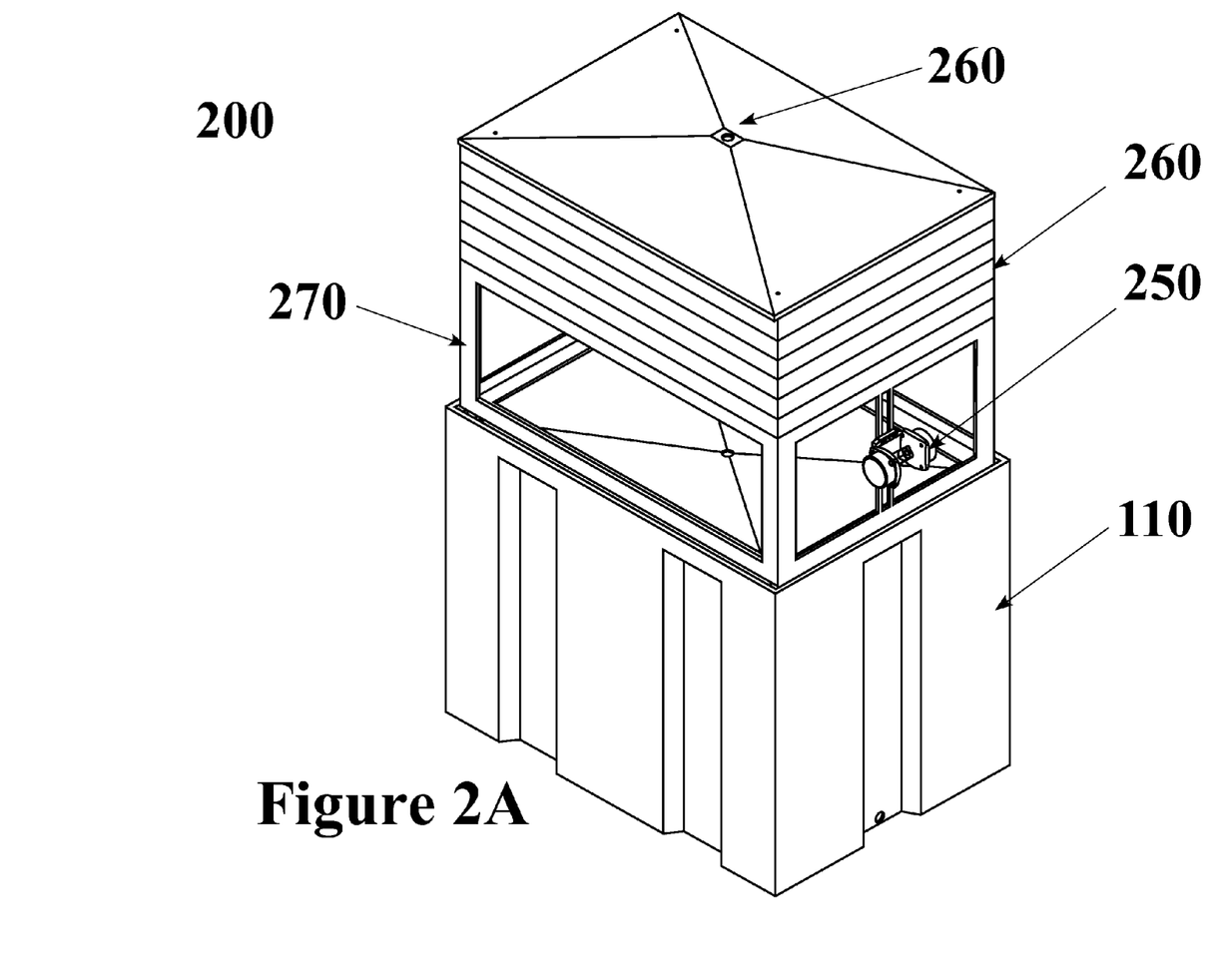
FIG. 2A is a schematic diagram of the vibrational sieve apparatus mounted on top of the 'run-off tank' tank, according to an embodiment of the invention.
Figure 2B:
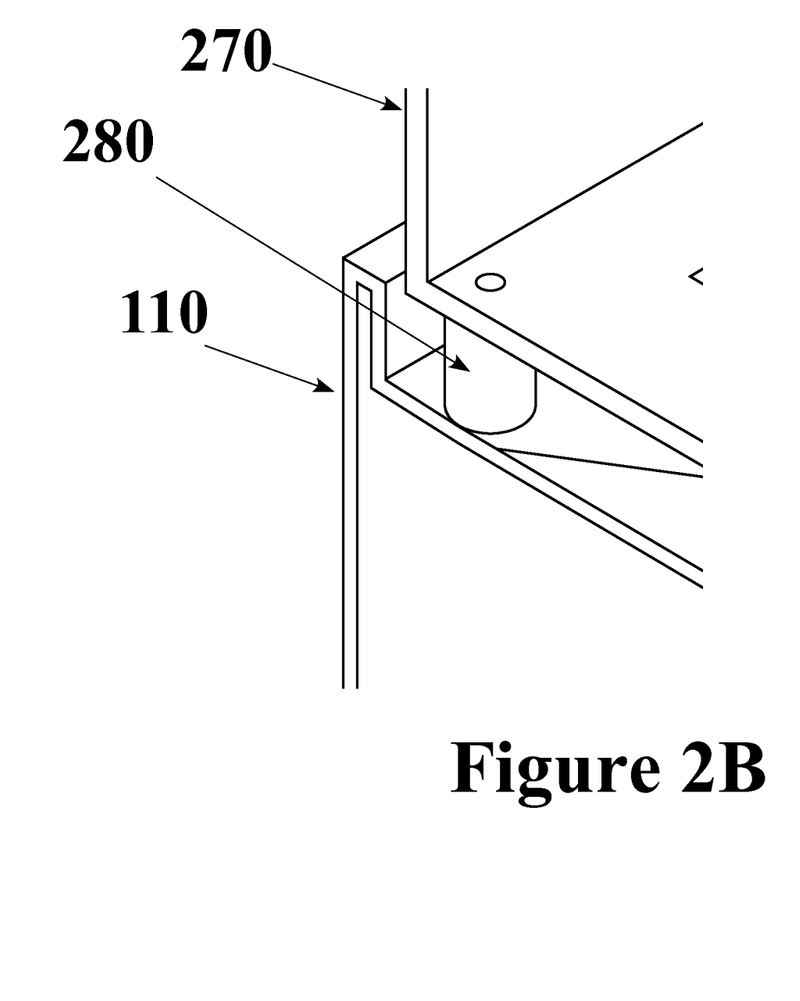
FIG. 2B is a schematic diagram showing the dampener supports connecting the frame of the vibrational sieve apparatus to the 'run-off tank', according to an embodiment of the invention.
Figures 3A, 3B:
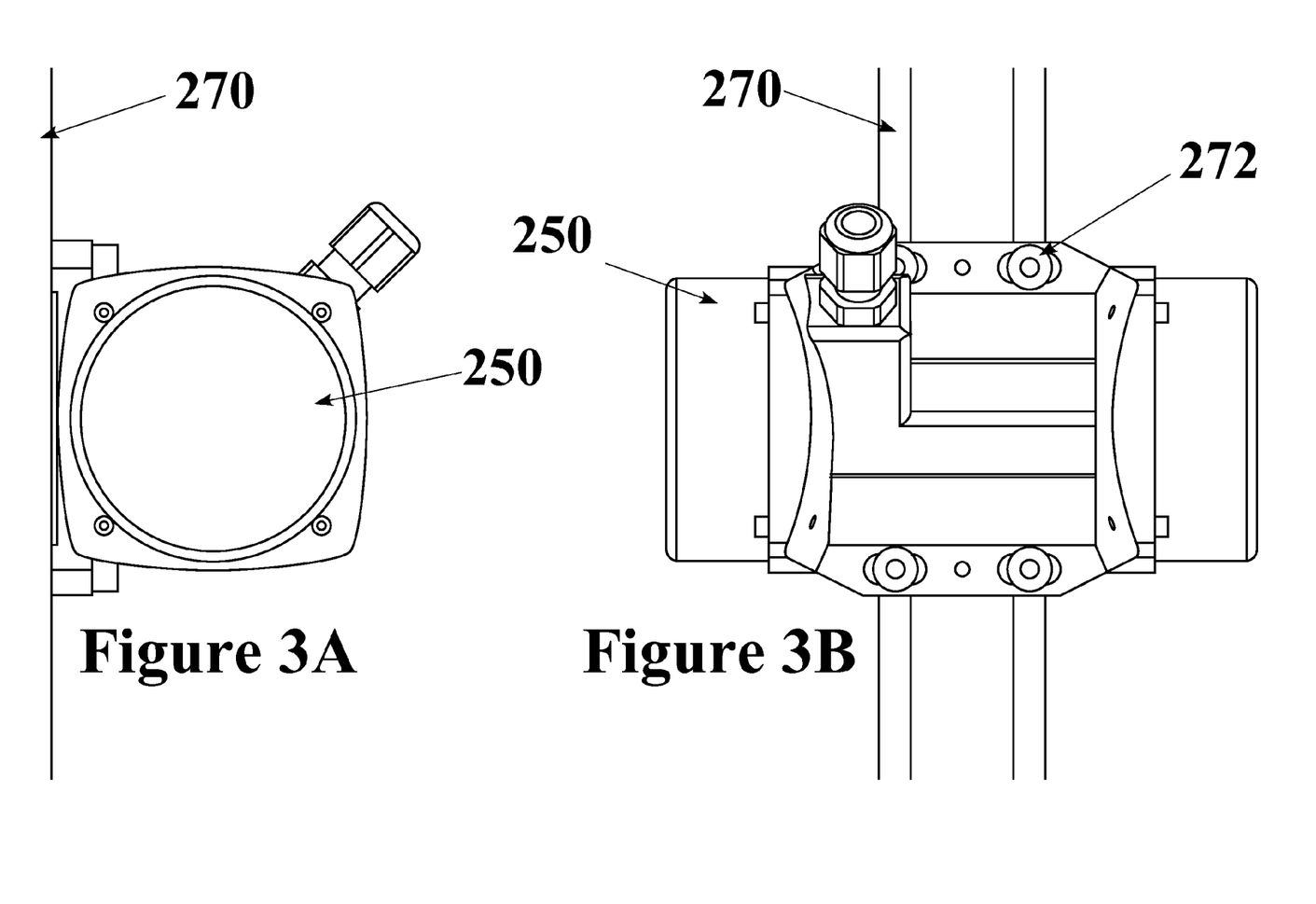
FIG. 3 shows the (A) side view and (B) frontal view of the motorvibrator, according to an embodiment of the invention.
Figure 4:
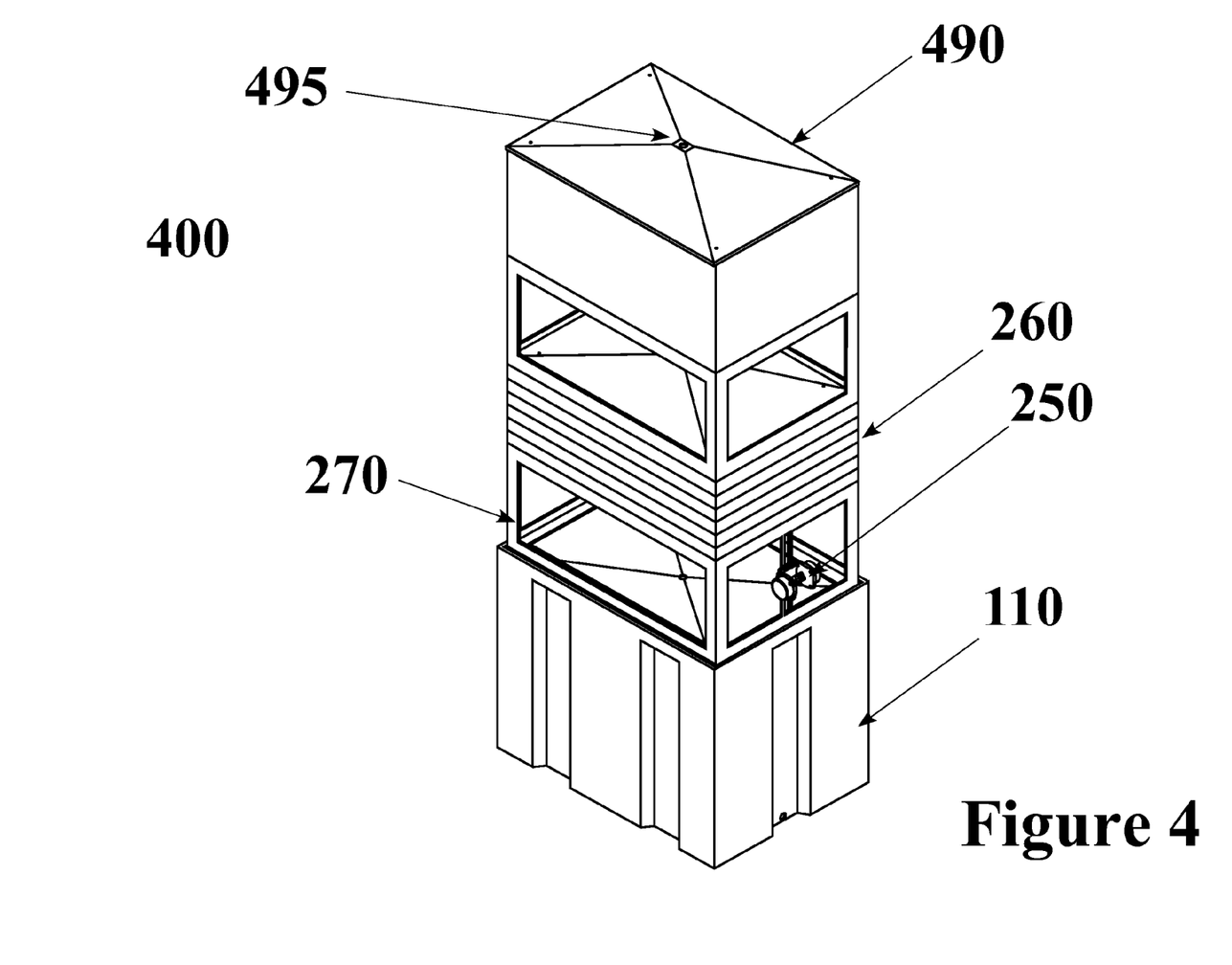
FIG. 4 is a schematic diagram of the vibrational sieve with a decanting tank containing the susceptible liquid mounted above the series of screens and subject to the vibrational forces, according to an embodiment of the invention.

FIGS. 1A and 1B show the 'run-off tank' 110 used to collect the decant (the portion of the susceptible liquid that is not retained). The run-off tank 110 can be made of plastic with a concave top 114 and a hole 112 to allow the decant to enter the run-off tank 110. A plug 116 at the bottom of the run-off tank allows the contents to be drained or transferred. FIG. 2A shows the vibrational sieve apparatus 200 with the motorvibrator 250 mounted onto a frame 270 mounted on top of the 'run-off tank' 110. In an embodiment, the run off tank 110 can be used to collect the portion of the susceptible liquid that is not retained on the screens 260 in the vibrational sieve apparatus. In an alternative embodiment, the 'run-off tank' 110 can be used to collect the decant from the screens (the portion of the susceptible liquid that is not retained on the screens in the vibrational sieve apparatus). The motovibrator 250 can be a Micro MVE41 electric vibrator configured to produce 143 ft/lbs of centrifugal force at 60 Hz (see info@olivibra.it) manufactured by Oli SpA, Medallo, Italy. The screens 260 can be attached to the frame 270 by way of bar clamps and/or ratchet straps. The frame can be made of aluminium or other metals. The run-off tank 110 is vibrationally isolated from the frame 270 by securing the frame to the run-off tank using plastic or rubber dampener feet 280. In an embodiment of the invention, the compound of interest in the susceptible liquid can be separated from impurities and collected in the run-off tank 110. The compound of interest can then be concentrated using freeze drying, evaporation, fractionation, distillation or other means. In an alternative embodiment of the invention, the compound of interest can be separated from impurities and collected on one or more of the screens 260. FIG. 2B is a schematic diagram showing the dampener supports 280 connecting the frame 270 of the vibrational sieve apparatus 200 to the run-off tank 110. FIG. 3 shows the (A) side view and (B) frontal view of the motorvibrator 250 mounted to the frame 270. The motovibrator can be mounted to the frame 270 using four (4) bolts 272. FIG. 4 is a schematic diagram of the vibrational sieve apparatus 400 with a separate holding tank 490 mounted on top of the series of screens 260. In an embodiment of the invention, the compound of interest in the susceptible liquid can be subjected to the vibrations induced by the motorvibrator 250 prior to being passed over the series of screens 260 and the decant collected in the run-off tank 110. An inlet 495 at the top of the holding tank 490 allows the holding tank 490 to be re-filled.

A susceptible liquid containing the organic trichomes can be prepared by mixing the organic material with water in a washing machine and carrying out a full wash cycle in the washing machine lasting eight to fifteen minutes. U.S. Pat. No. 5,452,594 to Choe entitled "Low Frequency Vibration Type Washing Machine" is explicitly incorporated by reference in its entirety. In an embodiment of the invention, the temperature of the water used to make up the susceptible liquid can be approximately 40-70 degrees F. In an embodiment of the invention, the temperature of the water used to make up the susceptible liquid can be approximately 33-40 degrees F. In this temperature range, approximately includes + or −5% of the temperature.

In an embodiment of the present invention, the vibrational sieve apparatus is used to collect glandular trichomes, resin ducts or subdermal oil glands extracted from Lamiaceae, *Pinus* or *Eucalyptus* material. A mesh zippered bag (200 micron mesh size) containing approximately 1 kg of the leaves or needles is immersed in a washing machine filled with 15 (U.S.) gallons of iced (approximately 4° C.) water, 20 lbs of ice, for 5-15 minutes to allow the material to hydrate. The washing machine is then turned on for a 5-15 minute standard wash cycle. At the end of the cycle, the water from the washing machine is transferred into a 60 (U.S.) gallon capacity cone bottom tank. The WM effluent is decanted after being allowed to stand for 10 minutes. The top 20 gallons is returned to the washing machines. The 10 gallon decant is transferred to the activated vibrating device. A stream of iced water (approximately 4° C.) flowing at less than 60 p.s.i is introduced to the device to wet the screens (comprising from lowest to highest: 25, 45, 75, 90, 120 and 200 microns) of the device. The 10 gallon decant is directed to the center of the vibrating (200 micron) screen (from where it is transferred to the 150 micron screen and so forth). The device effluent is returned to the washing machine in which the ice and the zippered bags remain. The material in the mesh zippered bags is removed and may be used for composting. Fresh material (containing a source of glandular trichomes, resin ducts or subdermal oil glands) is placed in the zippered bags which is placed in the washing machine allowing extraction of the essential oil from the fresh material. After the decant is transferred each screen is rinsed with a spray of iced (approximately 4° C.) water to remove pigments and other impurities. The material on the 200 micron mesh screens is discarded. The material on the 120 micron mesh screens is removed using a squeegee and duck pan and collected as a first (impure) fraction. The material on the 25, 45, 75 and 90 micron mesh screens is removed using the squeegee and duck pan and collected as a second fraction. The second fraction is placed on a 25 micron screen drying rack and distributed in thicknesses to less than 1 cm. The drying rack is placed in a 25° C. room with a flow of air from a fan directed at the screen for five to ten days.

An advantage of the vibrational sieve apparatus over extracting only into water is that the water, which is heavy, is not handled. Further, compared with alternative methods of isolating THC from aqueous based solutions this is a two step procedure where the purity of the collected material from the second sieving step is essentially independent of the first washing machine extraction step. Thus the first step can be extensive without reducing the purity collected in the vibrational sieving step.

Example 1 Tetrahydrocannabinol

In an embodiment of the present invention, the vibrational sieve apparatus was used to collect glandular trichomes extracted from *cannabis* leaves and buds. Initially, the sieves of the vibrational sieve apparatus were cleaned to insure that the mesh were free of organic matter by pressure spraying the screens with iced (approximately 4° C.) water (20 p.s.i.-100 p.s.i.). Next, three mesh zippered bags (200 micron mesh size) each bag containing 900 g of *cannabis* leaves and buds are immersed in a washing machine filled with 15 (U.S.) gallons of iced (approximately 4° C.) water, 20 lbs of ice, for 8 minutes to allow the *cannabis* leaves and buds to hydrate. The washing machine was then turned on for an 8 minute standard wash cycle. At the end of the cycle, the water from the washing machine was transferred into a 60 (U.S.) gallon capacity cone bottom tank. The WM effluent from two washing machines each running simultaneously was collected in the cone bottom tank. The WM effluent was then decanted after being allowed to stand for 10 minutes, with the top 40 gallons being discarded. A continuous stream of iced water (approximately 4° C.) flowing at less than 60 p.s.i was introduced to wet the screens (comprising from lowest to highest: 25, 45, 75, 90, 120 and 200 microns) of the vibrational sieve apparatus. The 20 gallon decant was next transferred to the vibrating sieve apparatus. The 20 gallon decant was pumped with a ⅙ h.p. pump through a ¾ inch tubing and directed to the center of the 200 micron screen (allowing the entire decant to be pumped in less than 1 minute). The device effluent was discarded. The material in the mesh zippered bags was removed and replaced with fresh *cannabis* leaves. The remaining steps of the above procedure were repeated an additional nine times. The material on the 200 micron mesh screens was discarded. The material on the 120 micron mesh screens was removed using a squeegee and duck pan and collected as fraction 1. The material on the 25, 45, 75 and 90 micron mesh screens was removed using the squeegee and duck pan and collected as fraction 2 (the most material was collected on the 75 micron mesh screen, which was also the size screen which produced the highest purity THC). Fraction 2 was placed on a 25 micron screen drying rack (30 cm×30 cm) and distributed so that the thickness of the fraction was less than 1 cm at any part of the drying rack. The drying rack was placed in a 25° C. room for seven days with free flow of air from above and below and a directed flow of air from a fan at the screen. The net weight of the material collected was 960 g. Chemical analysis using gas chromatography mass spectrometry carried out by a contract analytical laboratory indicated that dried fraction 2 had no fungal spores, and the THC was 90% pure.

Example 2 Mushroom Spores

In an embodiment of the present invention, the vibrational sieve apparatus was used to collect spores from mushrooms. Initially, the sieves of the vibrational sieve apparatus were cleaned to insure that the mesh were free of organic matter by pressure spraying the screens with iced (approximately 4° C.) water (>100 p.s.i.) and the screens were allowed to air dry. Next, mushrooms caps were dried and placed on the 200 micron screen and the vibrating device activated. After 5-30 minutes, the vibrating device was turned off and the material on the 200 micron mesh screens was removed. The material on the 25 micron mesh screens was removed and the spores collected and examined under a microscope (100×) to confirm that intact spores had been collected.

Example 3 Lavender Oil

The vibrational sieve apparatus was used to extract lavender oil glands and trichomes from lavender. Three mesh zippered bags (200 micron mesh size) each bag containing 1 kg of lavender are immersed in a washing machine filled with 15 (U.S.) gallons of iced (approximately 4° C.) water, 20 lbs of ice, for 8 minutes to allow the lavender to hydrate. The washing machine was then turned on for an 8 minute standard wash cycle. At the end of the cycle, the water from the washing machine was transferred into a 60 (U.S.) gallon capacity cone bottom tank. The WM effluent from the washing machine was collected in the cone bottom tank and this procedure was repeated three more times. The WM effluent was then decanted after being allowed to stand, with the top 40 gallons being discarded. A continuous stream of iced water (approximately 4° C.) flowing at less than 60 p.s.i was introduced to wet the screens (comprising from lowest to highest: 25, 45, 75, 90, 120 and 200 microns) of the vibrational sieve apparatus. The 20 gallon decant was next transferred to the vibrating sieve apparatus. The 20 gallon decant was pumped with a ⅙ h.p. pump through a ¾ inch tubing and directed to the center of the 200 micron screen (allowing the entire decant to be pumped in less than 1 minute). The device effluent was discarded. The material on the 200 micron mesh screens was discarded. The material on the 120 micron mesh screens was removed using a squeegee and duck pan and collected as fraction 1. The material on the 25, 45, 75 and 90 micron mesh screens was removed using the squeegee and duck pan and collected as fraction 2. Fraction 2 was placed in a Mason jar and allowed to dry in a 25° C. room for seven days. The product smelt of intense lavender and appeared as an opaque translucent oil.

Example 4 Rosemary Oil

The vibrational sieve apparatus was used to extract oil glands from rosemary. Mesh zippered bags (200 micron mesh size) containing 1 kg of rosemary are immersed in a washing machine filled with 15 (U.S.) gallons of iced (approximately 4° C.) water, 20 lbs of ice, for 8 minutes to allow the rosemary to hydrate. The washing machine was then turned on for an 8 minute standard wash cycle. At the end of the cycle, the water from the washing machine was transferred into a 60 (U.S.) gallon capacity cone bottom tank. The WM effluent from the washing machines was collected three more times in the cone bottom tank. The WM effluent was then decanted after being allowed to stand, with the top 40 gallons being discarded. A continuous stream of iced water (approximately 4° C.) flowing at less than 60 p.s.i was introduced to wet the screens (comprising from lowest to highest: 25, 45, 75, 90, 120 and 200 microns) of the vibrational sieve apparatus. The 20 gallon decant was next transferred to the vibrating sieve apparatus. The 20 gallon decant was pumped with a ⅙ h.p. pump through a ¾ inch tubing and directed to the center of the 200 micron screen (allowing the entire decant to be pumped in less than 1 minute). The device effluent was discarded. The material on the 200 micron mesh screens was discarded. The material on the 120 micron mesh screens was removed using a squeegee and duck pan and collected as fraction 1. The material on the 25, 45, 75 and 90 micron mesh screens was removed using the squeegee and duck pan and collected as fraction 2. Fraction 2 was placed in a Mason jar and allowed to dry in a 25° C. room for seven days. The product smelt strongly of rosemary and appeared as an opaque translucent somewhat chalky oil.

Example 5 Rose Oil

The system described in Example 1 was used to extract essential oil from rose petals. Mesh zippered bags (200 micron mesh size) each bag containing 1 kg of rose petals are immersed in a washing machine filled with 15 (U.S.) gallons of iced (approximately 4° C.) water, 20 lbs of ice, for 8 minutes to allow the rose petals to hydrate. The washing machine was then turned on for an 8 minute standard wash cycle. At the end of the cycle, the water from the washing machine was transferred into a 60 (U.S.) gallon capacity cone bottom tank. The WM effluent from the three more loads was collected in the cone bottom tank. The WM effluent was then decanted after being allowed to stand for 10 minutes, with the top 40 gallons being discarded. A continuous stream of iced water (approximately 4° C.) flowing at less than 60 p.s.i was introduced to wet the screens (comprising from lowest to highest: 25, 45, 75, 90, 120 and 200 microns) of the vibrational sieve apparatus. The 20 gallon decant was next transferred to the vibrating sieve apparatus. The 20 gallon decant was pumped with a ⅙ h.p. pump through a ¾ inch tubing and directed to the center of the 200 micron screen (allowing the entire decant to be pumped in less than 1 minute). The device effluent was discarded. The material on the 200 micron mesh screens was discarded. The material on the 120 micron mesh screens was removed using a squeegee and duck pan and collected as fraction 1. The material on the 25, 45, 75 and 90 micron mesh screens was removed using the squeegee and duck pan and collected as fraction 2. Fraction 2 was placed in a Mason jar and allowed to dry in a 25° C. room for seven days. The product smelt of rose and appeared as an opaque translucent oil.

Example 6 *Eucalyptus* Oil

The vibrational sieve apparatus was used to extract subdermal oil glands from *eucalyptus* leaves grown in Makawao Maui at an elevation of 3000 feet. Three mesh zippered bags (200 micron mesh size) each bag containing 1 kg of *eucalyptus* leaves are immersed in a washing machine filled with 15 (U.S.) gallons of iced (approximately 4° C.) water, 20 lbs of ice, for 8 minutes to allow the *eucalyptus* leaves to hydrate. The washing machine was then turned on for an 8 minute standard wash cycle. At the end of the cycle, the water from the washing machine was transferred into a 60 (U.S.) gallon capacity cone bottom tank. The WM effluent from the washing machine loaded with three additional replicate runs was collected in the cone bottom tank. The WM effluent was then decanted after being allowed to stand, with the top 40 gallons being discarded. A continuous stream of iced water (approximately 4° C.) flowing at less than 60 p.s.i was introduced to wet the screens (comprising from lowest to highest: 25, 45, 90, 110, 150 and 200 microns) of the vibrational sieve apparatus. The 20 gallon decant was next transferred to the vibrating sieve apparatus. The 20 gallon decant was pumped with a ⅙ h.p. pump through a ¾ inch tubing and directed to the center of the 200 micron screen (allowing the entire decant to be pumped in less than 1 minute). The device effluent was discarded. The material on the 200 micron mesh screens was discarded. The material on the 120 micron mesh screens was removed using a squeegee and duck pan and collected as fraction 1. The material on the 25, 45, 75 and 90 micron mesh screens was removed using the squeegee and duck pan and collected as fraction 2. Fraction 2 was placed in a Mason jar and allowed to dry in a 25° C. room for seven days. The product smelt of *eucalyptus* and appeared as an opaque translucent oil.

While the systems, methods, and devices have been illustrated by describing examples, it is not the intention of the applicants to restrict or in any way limit the scope of the appended claims to such detail. It is, of course, not possible to describe every conceivable combination of components or methodologies for purposes of describing the systems, methods, and devices provided herein. Additional advantages and modifications will readily be apparent to those skilled in the art. Therefore, the invention, in its broader aspects, is not limited to the specific details, the representative system and method or device shown and described. Accordingly, departures may be made from such details without departing from the spirit or scope of the applicant's general inventive concept. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

A susceptible liquid can be prepared by mixing *eucalyptus* leaves with water in a washing machine and carrying out a full wash cycle in the washing machine lasting ten to twelve minutes. The temperature of the water used to make up the susceptible liquid can be approximately 33-40 degrees F. In an embodiment of the invention, the temperature of the water used to make up the susceptible liquid can be approximately 31-33 degrees F. The wash cycle can be 'cold water'. The susceptible liquid in the washing machine can then be transferred to the vibrational sieve apparatus 200 and passed over the series of screens 260 while the motovibrator 250 is transferring vibrations to the screens 260. In an embodiment of the invention, the susceptible liquid is passed over two screens 260. In an embodiment of the invention, each of the two screens 260 has the same mesh size. In an alternative embodiment of the invention, the screen size of the two screens 260 is different. In an alternative embodiment of the invention, the susceptible liquid is passed over a series of ten screens 260. In an alternative embodiment of the invention, the susceptible liquid is passed over a series of six screens 260, orientated to allow gravity flow from the uppermost screen of the series of screens 260 to the lowest screen of the series of screens 260. In an embodiment of the invention, the uppermost screen can have a mesh size of approximately 500 microns. In an alternative embodiment of the invention, the uppermost screen of the series of screens 260 can have a mesh size of approximately 250 microns. In an embodiment of the invention, the lowermost screen of the series of screens 260 can have a mesh size of approximately 25 microns. In an alternative embodiment of the invention, the lowermost screen of the series of screens 260 can have a mesh size of approximately 5 microns. The decant from the susceptible liquid can be collected in the run-off tank 110. In an embodiment of the invention, the motorvibrator 250 can be tuned off and the screens 260 removed from the apparatus and the material caught by the screens 260 can be removed by either scraping and/or swabbing. In an alternative embodiment of the invention, after passing the susceptible liquid over the vibrating screens 260, the material that is collected can be further rinsed by passing water over the vibrating screens 260. In an embodiment of the invention, the rinsing step can be used to remove chlorophyll, other pigments, nutrients, gum, clay and/or lignous material from the *eucalyptus* oil trapped on the screens. The rinsing of the collected material can be carried out for one to ten minutes or until the decant shows no color. In an embodiment of the invention, the temperature of the rinse water can be approximately 40-70 degrees F. In an embodiment of the invention, the temperature of the rinse water can be approximately 33-40 degrees F. In an embodiment of the invention, the temperature of the rinse water can be approximately 31-33 degrees F. Then the motorvibrator 250 can be tuned off and the screens 260 removed and the material caught by the screens 260 can be removed by either scraping and/or swabbing.

Based on the effects of sonication, which can be used for evenly dispersing nano-particles in liquids, it was expected that the motorvibrational force can disperse the different components present in the susceptible liquid. In an unexpected result, the motovibrator increases the settling or separation of components present in the susceptible liquid. In an embodiment of the invention, reductions in the temperature of the susceptible liquid increase the mechanical settling and separation of components.

Parts of the description will be presented in data processing terms, such as data, selection, retrieval, generation, and so forth, consistent with the manner commonly employed by those skilled in the art to convey the substance of their work to others skilled in the art. As is well understood by those skilled in the art, these quantities (data, selection, retrieval, generation) take the form of electrical, magnetic, or optical signals capable of being stored, transferred, combined, and otherwise manipulated through electrical, optical, and/or biological components of a processor and its subsystems.

A method of isolating tetrahydrocannabinol (THC) containing trichomes from *cannabis* leaves comprising the steps of generating a susceptible liquid by mixing the *cannabis* leaves with water and vigorously pulsing, agitating and spinning, where the water is between a lower limit of approximately 3 degrees Celsius and an upper limit of approximately 6 degrees Celsius. Vibrating an apparatus including a container mounted above the apparatus and at least a plurality of collection screens, where the plurality of collection screens have different size mesh. Transferring the susceptible liquid to the container. Decanting the susceptible liquid in the container and removing the supernatant. Distributing the susceptible liquid over the plurality of collection screens. Rinsing the plurality of collection screens with water and collecting the THC containing trichomes retained on one or more of the plurality of collection screens, where the THC containing trichomes are between: a lower limit of approximately 70 percent and an upper limit of approximately 90 percent THC, where the yield of THC is between a lower limit of approximately 1 percent w/w and an upper limit of approximately 5 percent w/w.

A method of isolating tetrahydrocannabinol (THC) containing trichomes from *cannabis* leaves comprising the steps of generating a susceptible liquid by mixing the *cannabis* leaves with water and vigorously pulsing, agitating and spinning, where the water is between a lower limit of approximately 3 degrees Celsius and an upper limit of approximately 10 degrees Celsius. Vibrating an apparatus including a container mounted above the apparatus and at least a plurality of collection screens, where the plurality of collection screens have different size mesh. Transferring the susceptible liquid to the container. Decanting the susceptible liquid in the container and removing the supernatant. Distributing the susceptible liquid over the plurality of collection screens. Rinsing the plurality of collection screens with water and collecting the THC containing trichomes retained on one or more of the plurality of collection screens, where the THC containing trichomes are between: a lower limit of approximately 60 percent and an upper limit of approximately 80 percent THC, where the yield of THC is between a lower limit of approximately 1 percent w/w and an upper limit of approximately 4 percent w/w.

A method of isolating tetrahydrocannabinol (THC) containing trichomes from *cannabis* leaves comprising the steps of generating a susceptible liquid by mixing the *cannabis* leaves with water and vigorously pulsing, agitating and spinning, where the water is between a lower limit of approximately 1 degrees Celsius and an upper limit of approximately 5 degrees Celsius. Vibrating an apparatus including a container mounted above the apparatus and at least a plurality of collection screens, where the plurality of collection screens have different size mesh. Transferring the susceptible liquid to the container. Decanting the susceptible liquid in the container and removing the supernatant. Distributing the susceptible liquid over the plurality of collection screens. Rinsing the plurality of collection screens with water and collecting the THC containing trichomes retained on one or more of the plurality of collection screens, where the THC containing trichomes are between: a lower limit of approximately 60 percent and an upper limit of approximately 80 percent THC, where the yield of THC is between a lower limit of approximately 1 percent w/w and an upper limit of approximately 3 percent w/w.

Various operations will be described as multiple discrete steps in turn, in a manner that is most helpful in understanding the present invention; however, the order of description should not be construed as to imply that these operations are necessarily order dependent.

Various embodiments will be illustrated in terms of exemplary classes and/or objects in an object-oriented programming paradigm. It will be apparent to one skilled in the art that the present invention can be practiced using any number of different classes/objects, not merely those included here for illustrative purposes.

The invention is illustrated by way of example and not by way of limitation in the figures of the accompanying drawings in which like references indicate similar elements. It should be noted that references to 'an' or 'one' embodiment in this disclosure are not necessarily to the same embodiment, and such references mean at least one.

In various embodiments of the invention, the isolated compound is of at least one state selected from the group consisting of solid phase, liquid phase, and gas phase. In various embodiments of the invention, the isolated compound is of biological origin. In various embodiments of the invention, the isolated compound is of non-biological origin.

In various embodiments of the invention, the isolated compound is selected from the group consisting of a pharmaceutical product, a pharmaceutical ingredient, a food, a food ingredient, a toxin, a drug, an explosive, a bacterium, an oil, a petrochemical substitute and a biological tissue.

A device for purifying a compound comprising a frame, two or more screens mounted on the frame, a vibration source adapted to produce a vibration, a mount adapted to secure the vibration source to the frame and transfer the vibration at least to the two or more screens and a spreader adapted to flow a first susceptible liquid containing the compound over the two or more screens, where the compound is collected on one or more of the two or more screens.

What is claimed is:

1. A method of isolating tetrahydrocannabinol (THC)-containing trichomes from *cannabis* leaves comprising the steps of:
    (a) agitating *cannabis* leaves immersed in water to generate a susceptible liquid containing a plurality of THC-containing trichomes in a first container;
    (b) transferring the susceptible liquid to a second container;
    (c) vibrating the second container positioned above two or more collection screens, where a first screen of the two or more collection screens has a larger micron size than a second screen of the two or more collection screens, where the two or more collection screens and the second container are vibrated with a vibration frequency between:
    a lower limit of approximately 50 Hz; and
    an upper limit of approximately 70 Hz;
    (d) decanting the susceptible liquid in the second container and removing the supernatant from the decant;
    (e) distributing the decant over at least the first screen;
    (f) distributing the decant flowing through the first screen over at least the second screen;
    (g) rinsing the two or more collection screens with water;
    (h) discarding material collected on the first screen; and
    (i) isolating one or more of the plurality of THC-containing trichomes on at least the second screen.

2. The method of claim 1, where the purity of the one or more of the THC-containing trichomes is between:
    a lower limit of approximately 80 percent; and
    an upper limit of approximately 95 percent THC.

3. The method of claim 1, where THC yield is between:
    a lower limit of approximately 1 percent w/w; and
    an upper limit of approximately 10 percent w/w.

4. The method of claim 1, where the two or more collection screens have mesh sizes varying between:
    a lower limit of approximately 25 microns; and
    an upper limit of approximately 120 microns.

5. The method of claim 1, where *cannabis* leaves are not transferred to the second container.

6. The method of claim 1, where the water is between:
    a lower limit of approximately 1 degree C.; and
    an upper limit of approximately 4 degrees C.

7. The method of claim 1, where the first container is agitated at vibrational frequency greater than 70 Hz.

8. The method of claim 1, where the decant passes through the two or more collection screens, where the THC-containing trichomes are retained on one or more of the two or more collection screens.

9. The method of claim 1, where a third screen of the two or more collection screens has a smaller micron size than the second screen of the two or more collection screens.

10. The method of claim 1, where the first screen is approximately 250 micron screen size.

11. The method of claim 1, where the first screen is approximately 120 micron screen size.

12. The method of claim 9, where the one or more of the THC-containing trichomes collected on the third screen is collected.

13. The method of claim 1, where the two or more collection screens include a third screen of approximately 90 micron screen size.

14. The method of claim 13, where the second screen has a larger micron size than the third screen.

15. The method of claim 13, where the one or more of the THC-containing trichomes collected on the third screen is collected as a separate fraction.

16. The method of claim 1, where the second container is vibrated at 143 ft/lbs of centrifugal force at 60 Hz.

\* \* \* \* \*